(12) United States Patent
Whitekettle et al.

(10) Patent No.: US 8,784,659 B2
(45) Date of Patent: Jul. 22, 2014

(54) METHOD FOR CONTROLLING MICROBIAL BIOFILM IN AQUEOUS SYSTEMS

(75) Inventors: Wilson Kurt Whitekettle, Jamison, PA (US); Gloria Jean Tafel, Doylestown, PA (US); Qing Zhao, Shanghai (CN); Linna Wang, Shanghai (CN); Dorothy Reynolds, North Wales, PA (US); Paul Frail, Cherry Hill, NJ (US); Juan Jiang, Shanghai (CN); David M. Polizzotti, Yardley, PA (US)

(73) Assignee: General Electric Company, Schenectady, NY (US)

( * ) Notice: Subject to any disclaimer, the term of this patent is extended or adjusted under 35 U.S.C. 154(b) by 824 days.

(21) Appl. No.: 12/892,490

(22) Filed: Sep. 28, 2010

(65) Prior Publication Data

US 2011/0052656 A1 Mar. 3, 2011

Related U.S. Application Data

(63) Continuation-in-part of application No. 11/835,722, filed on Aug. 8, 2007, now Pat. No. 7,824,557, which is a continuation-in-part of application No. PCT/US2008/065197, filed on May 30, 2008.

(51) Int. Cl.
*C02F 1/50* (2006.01)

(52) U.S. Cl.
USPC ........... 210/606; 210/631; 210/632; 210/755; 210/756; 210/764

(58) Field of Classification Search
USPC ......... 210/600, 632, 749, 764, 606, 631, 755, 210/756; 424/421, 637, 618, 667, 661, 616, 424/680, 718, 417; 514/740, 365, 646, 516, 514/634, 241, 139, 675, 561, 223.8, 372
See application file for complete search history.

(56) References Cited

U.S. PATENT DOCUMENTS 4,561,981 A 12/1985 Characklis
5,008,109 A * 4/1991 Tin .............................. 428/402.2

(Continued)

FOREIGN PATENT DOCUMENTS

AU 1 561 901 3/1980
CN 1369202 A 9/2002

(Continued)

OTHER PUBLICATIONS

Third Office Action issued Mar. 15, 2013 for Chinese Patent Application No. 200880111492.4 filed May 30, 2008.

(Continued)

*Primary Examiner* — Lucas Stelling
(74) *Attorney, Agent, or Firm* — Wegman, Hessler & Vanderburg (57) ABSTRACT

A process has been found which increases the efficiency and effectiveness of introducing antimicrobial compounds into complex biofilm matrices through the use of liposome carriers, thereby removing the biofouling in industrial water bearing systems, including piping, heat exchanges, condensers, filtration systems and fluid storage tanks. According to one embodiment of the invention, antimicrobial compound containing liposomes are added to water systems prone to biofouling and biofilm formation. The liposomes, being similar in composition to microbial membranes or cells, are readily incorporated into the existing biofilm. Once the antimicrobial compound containing liposomes become entrained with the biofilm matrix, the decomposition or programmed disintegration of the liposome proceeds. Thereafter, the biocidal aqueous core is released to react directly with the biofilm encased microorganisms. Upon the death of the organisms, the polysaccharide/protein matrix decomposes and thereby results in reduced fouling of the water bearing system, resulting in increased heat transfer, increased flux, less deposit of colloidal and particulate solids and dissolved organics on the surface of the microfiltration membrane, thereby reducing the frequency and duration of the membrane cleaning and ultimate replacement.

19 Claims, 2 Drawing Sheets

(56) References Cited

U.S. PATENT DOCUMENTS

| | | | |
|---|---|---|---|
| 5,063,213 A | 11/1991 | Whitekettle et al. | |
| 5,081,134 A | 1/1992 | Whitekettle et al. | |
| 5,093,357 A | 3/1992 | Whitekettle et al. | |
| 5,164,096 A | 11/1992 | Nunn | |
| 5,411,666 A | 5/1995 | Hollis et al. | |
| 5,464,696 A * | 11/1995 | Tournier et al. | 428/403 |
| 5,512,213 A | 4/1996 | Paterson | |
| 5,547,939 A | 8/1996 | Selsted | |
| 5,569,464 A | 10/1996 | Endo et al. | |
| 5,789,239 A | 8/1998 | Eyers et al. | |
| 5,807,572 A | 9/1998 | Kim et al. | |
| 5,955,486 A | 9/1999 | Mattox | |
| 6,008,238 A | 12/1999 | El A'mma et al. | |
| 6,267,897 B1 | 7/2001 | Robertson et al. | |
| 6,267,979 B1 | 7/2001 | Raad et al. | |
| 6,498,862 B1 | 12/2002 | Pierson et al. | |
| 6,579,541 B2 | 6/2003 | Antelman | |
| 6,759,040 B1 | 7/2004 | Manyak et al. | |
| 6,811,711 B2 | 11/2004 | Unhoch et al. | |
| 6,998,049 B1 | 2/2006 | Meyer et al. | |
| 7,008,545 B2 | 3/2006 | Cronan, Jr. et al. | |
| 7,338,663 B2 | 3/2008 | Li et al. | |
| 7,491,409 B1 | 2/2009 | Meers et al. | |
| 7,824,557 B2 * | 11/2010 | Whitekettle et al. | 210/764 |
| 2007/0196359 A1 | 8/2007 | Walter et al. | |
| 2008/0102111 A1 | 5/2008 | Imanaka | |
| 2001/0177147 | 7/2011 | Hunter et al. | |

FOREIGN PATENT DOCUMENTS

| | | |
|---|---|---|
| WO | WO2009020689 | 2/2009 |
| WO | WO2009020694 | 2/2009 |

OTHER PUBLICATIONS

Government President, College Entrance Examination Technician Examination Institute, Environmental Microbiology Intensive No. 097127547 CSYZ2, Taipei, Taiwan, 3 pages, 1996.

Ling, "Surface Active Agent and Nanotechnology", Surfactant and Nanotechnology, Collections of Surfactant Application Technology, Chemical Industry Press, Chemistry and Applied Chemistry Publication Center, Beijing, China Feb. 2004, pp. 3-10, Table of Contents, p. 103, and pp. 299-300.

Jones, "Use of Liposomes to Deliver Bactericides to Bacterial Biofilms", Methods in Enzymology, vol. 391, 2005, pp. 211-228.

Smith, "Biofilms and Antibiotic Therapy: Is There a Role for Combating Bacterial Resistance by the Use of Novel Drug Delivery Systems?" Advance Drug Delivery Reviews, vol. 57, 2005, pp. 1539-1550.

\* cited by examiner

FIG. 1 Liposome/MBT biocidal efficacy on Pseudomonas fluoresens biofilm

FIG. 2 Liposome/MBT biocidal efficacy on Pseudomonas fluoresens biofilm

FIG. 3 MBT-Liposome Effecacy vs. Pseudomonas fluorescens Biofilm

FIG. 4 DGH-Liposome Efficacy vs. Pseudomonas fluorescens Biofilm

METHOD FOR CONTROLLING MICROBIAL BIOFILM IN AQUEOUS SYSTEMS

CROSS REFERENCE TO RELATED APPLICATIONS

The present application is a continuation in part application of U.S. patent application Ser. No. 11/835,722 filed Aug. 8, 2007 and of International Patent Application No. PCT/US2008/065197 filed May 30, 2008. The contents of both of the aforementioned applications are hereby incorporated by reference herein.

FIELD OF INVENTION

The field of the invention relates to destroying microbial biofilms in aqueous systems. More particularly, the invention relates to the use of antimicrobial or other compounds to destroy microbial biofilm.

BACKGROUND OF THE INVENTION

Many different types of industrial or commercial operations rely on large quantities of water for various reasons, such as for cooling systems, or produce large quantities of wastewater, which need to be treated. These industries include, but are not limited to, agriculture, petroleum, chemical, pharmaceutical, mining, metal plating, textile, brewing, food and beverage processing, and semiconductor industries. Naturally occurring biofilms are continuously produced and often accumulate on numerous structural or equipment surfaces or on natural or biological surfaces. In industrial settings, the presence of these biofilms causes a decrease in the efficiency of industrial machinery, requires increased maintenance and presents potential health hazards. An example is the surfaces of water cooling towers which become increasingly coated with microbially produced biofilm slime which constricts water flow and reduces heat exchange capacity. Specifically, in flowing or stagnant water, biofilms can cause serious problems, including pipeline blockages, corrosion of equipment by growth of underfilm microbes and the growth of potentially harmful pathogenic bacteria. Water cooling tower biofilms may form a harbor or reservoir that perpetuates growth of pathogenic microorganisms such as *Legionella pneumophila*.

Food preparation lines are routinely plagued by biofilm build-up both on the machinery and on the food product where biofilms often include potential pathogens. Industrial biofilms are complex assemblages of insoluble polysaccharide-rich biopolymers, which are produced and elaborated by surface dwelling microorganisms. More particularly, biofilms or microbial slimes are composed of polysaccharides, proteins and lipopolysaccharides extruded from certain microbes that allow them to adhere to solid surfaces in contact with water environments and form persistent colonies of sessile bacteria that thrive within a protective film. The film may allow anaerobic species to grow, producing acidic or corrosive conditions. To control these problems, processes and antimicrobial products are needed to control the formation and growth of biofilms Control of biofilms involves preventing microbial attachment and/or removing existing biofilms from surfaces. While removal in many contexts is accomplished by short cleansing treatments with highly caustic or oxidizing agents, the most commonly used materials to control biofilms are biocides and dispersants. In U.S. Pat. No. 5,411,666, a method of removing a biofilm or preventing buildup of a biofilm on a solid substrate is taught, that comprises a combination of at least two biologically produced enzymes, such as an acidic or alkaline protease and a glucoamylase or alpha amylase and at least one surfactant. U.S. Pat. No. 6,759,040 teaches a method for preparing biofilm degrading, multiple specificity, hydrolytic enzyme mixtures that are targeted to remove specific biofilms. U.S. Pat. No. 6,267,897, relates to a method of inhibiting biofilm formation in commercial and industrial water systems by adding one or more plant oils to the system.

However, although the biocides are effective in controlling dispersed microorganism suspensions, i.e., planktonic microbes, but biocides do not work well against sessile microbes, the basis of biofilms. This is due to the fact that biocides have difficulty penetrating the polysaccharide/protein slime layers surrounding the microbial cells. Thicker biofilms see little penetration of biocides and poor biocide efficacy is the result. As disclosed in the prior art, one method of trying to better control biofilms has been the addition of dispersants and wetting agents to biocide compositions to enhance biocide efficacy. Biodispersants may operate to keep planktonic microbes sufficiently dispersed that they do not agglomerate or achieve the local densities necessary to initiate the extracellular processes responsible for anchoring to a surface, or initiating film- or colony-forming mechanisms. As components in biocidal treatment formulations, these biodispersants have helped in opening channels in the biofilm to allow better permeability of the toxic agents and to better disperse the microbial aggregates and clumps that have been weakened and released from the surfaces. However, biodispersants have proven to be more effective in preventing initial biofilm formation than in removing existing biofilms. In many cases, the activity of biodispersants has been responsible for only 25 to 30% biomass removal from biofouled surfaces, even when used in conjunction with a biocidal agent.

Therefore, a clear need still exists for an efficient and effective means for penetrating existing biofilms and killing biofilm organisms with a biofilm matrix, decrease the fouling of the microfiltration systems, providing less frequent cleaning and/or replacement and would enhance the overall filtration process.

SUMMARY OF THE INVENTION

A process has been found which increases the efficiency and effectiveness of introducing antimicrobial compounds into complex matrices, through the use of liposome carriers, thereby removing the fouling in industrial water conduit systems, including piping, heat exchangers, condensers, filtration systems and media, and fluid storage tanks.

According to one embodiment of the invention, liposomes containing an antimicrobial agent, such as a hydrophilic biocide, are added to a water system prone to biofouling and biofilm formation. The liposomes, being similar in composition to the microbial surface or to material on which the microbes feed, are readily incorporated into the existing biofilm. Once the liposomes become entrained with the biofilm matrix, digestion, decomposition or programmed disintegration of the liposome proceeds, releasing the antimicrobial agent, or biocidal aqueous core reacts locally with the biofilm-encased microorganisms. Upon the death of the organisms, the polysaccharide/protein matrix cannot be replenished and decomposes and thereby results in reduced bio fouling of the water bearing system. Depending on the particular aqueous system involved, this biofilm removal or destruction therefore results in increased heat transfer (industrial heat exchanger), increased flux (filter or filtration membrane), less deposit of colloidal and particulate solids and dissolved organics on the surface of the microfiltration membrane, thereby reducing the frequency and duration of the membrane cleaning and ultimate replacement, or general reduction of corrosive surface conditions in pipelines, tanks, vessels or other industrial equipment.

The various features of novelty that characterize the invention are pointed out with particularity in the claims annexed to and forming a part of this disclosure. For a better understanding of the invention, its operating advantages and benefits obtained by its uses, reference is made to the accompanying drawings and descriptive matter. The accompanying drawings are intended to show examples of the invention. The drawings are not intended as showing the limits of all of the ways the invention can be made and used. Changes to and substitutions of the various components of the invention can of course be made. The invention resides as well in sub-combinations and sub-systems of the elements described, and in methods of using them.

BRIEF DESCRIPTION OF THE DRAWINGS

Refer now to the figures, which are meant to be exemplary and not limiting, and wherein like elements are numbered alike, and not all numbers are repeated in every figure for clarity of the illustration.

DETAILED DESCRIPTION OF EXEMPLARY EMBODIMENTS

While the present invention is described with references to illustrative examples and preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but also all that fall within the scope of the appended claims.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus.

A process has been found which increases the efficiency and effectiveness of introducing antimicrobial compounds into complex matrices through the use of liposome carriers, thereby removing the fouling in industrial water conduit systems, including piping, heat exchangers, condensers, filtration systems and media, and fluid storage tanks.

According to one embodiment of the invention, liposomes containing a biocidal or antimicrobial agent or compound are added to an aqueous system prone to biofouling and biofilm formation. The liposomes, being similar in composition to microbial membranes or cells, are readily incorporated into the existing biofilm. Once the antimicrobial compound-containing liposomes diffuse into, adsorb or otherwise become entrained with the biofilm matrix, the decomposition or programmed disintegration of the liposome proceeds. That is lipid decomposition and biocide release can be programmed to occur by making the lipid matrix sensitive to pH, redox potential, $Ca^{+2}$ concentration, or other changes. Thereafter, the biocidal component (which may be concentrated in the aqueous core of the liposome or in the lipid membrane portion of the liposome, is released to react directly with the biofilm-encased microorganisms. Thus, rather than adding a biocide at high levels to the bulk water system, a small quantity of liposome-encased biocide is taken up by the biofilm or by free (planktonic) organisms, and degradation of the liposome releases the biocide locally in or at the target organisms or their film matrix niche. The biocide thus attains a high concentration locally to kill the target organisms, and upon the death of the organisms, the polysaccharide/protein matrix that forms the biofilm cannot be regenerated and decomposes, and thereby results in reduced fouling of the water bearing system, resulting in increased heat transfer, increased flux, less deposit of colloidal and particulate solids and dissolved organics on the surface of the microfiltration membrane, thereby reducing the frequency and duration of the membrane cleaning and ultimate replacement or other benefits.

Liposomes, or lipid bodies, are systems in which lipids are added to an aqueous buffer to form vesicles, structures that enclose a volume. More specifically, liposomes are microscopic vesicles, most commonly composed of phospholipids and water. When properly mixed, the phospholipids arrange themselves into a bilayer or multilayers, very similar to a cell membrane, surrounding an aqueous volume core. Liposomes can be produced to carry various compounds or chemicals within the aqueous core, or the desired compounds can be formulated in a suitable carrier to enter the lipid layer(s). Liposomes can be produced in various sizes and may be manufactured in submicron to multiple micron diameters. The liposomes may be manufactured by several known processes. Such processes include, but are not limited to, controlled evaporation, extrusion, injection, microfluid processors and rotor-stator mixers. Liposomes can be produced in diameters ranging from about 10 nanometers to greater than about 15 micrometers. When produced in sizes from about 100 nanometers to about 2 micrometer sizes the liposomes are very similar in size and composition to most microbial cells. The biocide or antimicrobial compound-containing liposomes should be produced in sizes that mimic bacterial cells, from about $0.05\mu$ to about $15\mu$, or alternately, about $0.1\mu$ to $10.0\mu$.

Effective amounts of the biocide containing liposome is introduced into an aqueous system which is prone to biofouling and biofilm formation, or can be introduced into systems that already exhibit signs of biofouling or biofilm formation. The effective amount will vary according to the antimicrobial compound or biocide, and the aqueous system to which it is added, but one embodiment provides from about 0.01 ppm to about 20 ppm, with an alternative of from about 0.05 to about 15 ppm, alternately from about 0.05 to about 0.5 ppm. The liposomes, being similar in composition to microbial membranes, or cells, are readily incorporated into the existing biofilm and become entrained within the biofilm matrix. Upon the decomposition or programmed disintegration of the liposome, the biocidal compound in the aqueous core or bound in the membrane is released to react directly with the biofilm encased microorganisms. Upon the death of the organisms, the polysaccharide/protein matrix will rapidly decompose, freeing the surface from contaminating microbes. A principal feature of the invention is that the liposomes of the present invention constitute extremely small hydrophobic bodies that may readily survive in and disperse in an aqueous system, yet will adsorb to or penetrate a biofilm and preferentially target or be targeted by the microbes that inhabit, constitute or sustain the biofilm. As such, they deliver a biocidal agent directly to the microbes or biofilm, resulting in effective locally biocidal level of activity, without requiring that the aqueous system as a whole sustain a high dose. Thus, where conventional biofilm treatment may require dosing with a bulk biocidal chemical at a certain level, delivery via liposome may be dosed at levels an order of magnitude or more lower in the aqueous system, yet still achieve, or build up to a level that effectively controls or removes biofilm. Indeed, while the terms "antimicrobial" or "biocidal" have been employed to describe the agent carried by the liposome, these agents need not be the highly bioactive materials normally understood by those terms, but may include a number of relatively harmless materials that become highly effective simply by virtue of their highly localized release. Thus, for example, surfactants or harmless salts, when released locally, may affect the normal action of extracellular colony-forming secretions, and are to be included as antimicrobial or biocidal agents for purposes of the invention, and the same mechanism may be employed to deliver other treatment chemicals to the targeted biofilm sites.

Aqueous systems that can be treated by this method include, but are not limited to, potable and non-potable water distribution systems, cooling towers, boiler systems, showers, aquaria, sprinklers, spas, cleaning baths, air washers, pasteurizers, air conditioners, fluid transporting pipelines, storage tanks, ion exchange resins, food and beverage processing lines, metalworking fluid baths, coal and mineral slurries, metal leaching fluids, wastewater treatment facilities, mollusk control, acid mine drainage, or any application prone to biofouling by microbial species. Application such as oil pipelines, where biofilms form in stagnant or pooled aqueous sumps or lenses along the conduit system, may also be effectively treated.

Additional applications for liposome delivery of a treatment chemical are anti-corrosion treatments for equipment generally, delivery of hormone, vitamin or antioxidant treatments or antibiotic and gene therapies for medical or veterinary purposes, delivery of pesticides for agriculture and commercial home uses, effective formulations of food additives and preservatives, targeted delivery for chemical and biological detection systems, color and flavor enhancement, odor control and aquatic pest management.

A variety of known biocides or antimicrobial compounds can be incorporated into the liposomes. Some examples of antimicrobial compounds that can be used include, but are not limited to, non-oxidizing, oxidizing, biodispersant, and molluscicide antimicrobial compounds, and combinations thereof. More specifically, suitable antimicrobial compounds, include, but are not limited to, 2-bromo-2-nitropropane-1,3-diol, 5-chloro-2-methyl-4-isothiazolin-3-one/2-methyl-4-isothiazolin-3-one, n-alkyl-dimethylbenzylammonium chloride, 2,2-dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium salt, 4,5-dichloro-1,2-dithiol-3-one, sodium dimethyldithiocarbamate, disodium ethylenebisdithiocarbamate, Bis(trichloromethyl) sulfone, 3,5-dimethyl-tetrahydro-2H-1,3,5-thiadiazine-2-thione, 1,2-benzisothiazolin-3-one, decylthioethylamine hydrochloride, copper sulfate, silver nitrate, colloidal silver, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, dibromo, dicyano butane and combinations thereof.

Effective amounts of the biocide incorporated into the liposome would depend on the biocide or agent incorporated therein. However effective amounts include from about 0.05 to about 5 grams biocide active per gram lipid, or alternately about 0.1 to about 2 grams biocide active per gram lipid.

Liposomes of the present invention may be created as multi-layer bodies, in which one or more additional layers are provided to enhance the stability of the liposomes or to effectuate a programmed release of the underlying lipid body and contents. Thus, not unlike the technology used to encapsulate medicines for intracorporal delivery, the additional layers may include a protective layer that is hydrolysed or otherwise breaks down over time to provide a sustained release or longer lifetime of the underlying liposome. Such additional layer may additionally or alternatively include an encapsulating polymer that selectively breaks down when the multi-layer liposome encounters a low-pH environment, like the corrosive high acidity environment that may develop beneath a biofilm. A layer may also be compounded to be vulnerable to sulfur-fixing bacteria, causing the liposome to specifically release its biocide in proximity to these corrosive organisms often present in a waste or pipeline system. Furthermore, several such layers may be employed to assure a sufficient lifetime of the liposome, preferably on the order of several days as well as an ability to target a specific niche or environment in the biofilm. This assures that the liposomes will effectively encounter the target organisms or biofilm colonies and deliver their biocides thereto. The lipid material itself may be treated to provide enhanced resistance to hydrolysis or decay, or the added layers may be formed of various hardenable or cross-linkable oils or polymers.

The invention will now be described with respect to certain examples that are merely representative of the invention and should not be construed as limiting thereof.

EXAMPLE

The invention is illustrated in the following non-limiting examples, which are provided for the purpose of representation, and are not to be construed as limiting the scope of the invention. All parts and percentages in the examples are by weight unless indicated otherwise.

Liposomes (150 nanometers average diameter) were created that incorporated the biocide methylene bis thiocyanate (MBT), a US EPA registered biocide active ingredient. The liposomes were then placed in microtiter plates that had microbial biofilms coating them. The microbe inhibiting efficacy of the MBT-liposomes was then compared with non-liposomal MBT when used at the same MBT concentrations. The liposomes containing MBT penetrated the biofilm and inhibited the biofilm organisms much more effectively than the non-liposomal MBT (control MBT) solution.

Two MBT containing liposomes were created designated MBT-1 (155 nm average diameter) and MBT-2 (137 nm average diameter) in the results.

Figure 1:
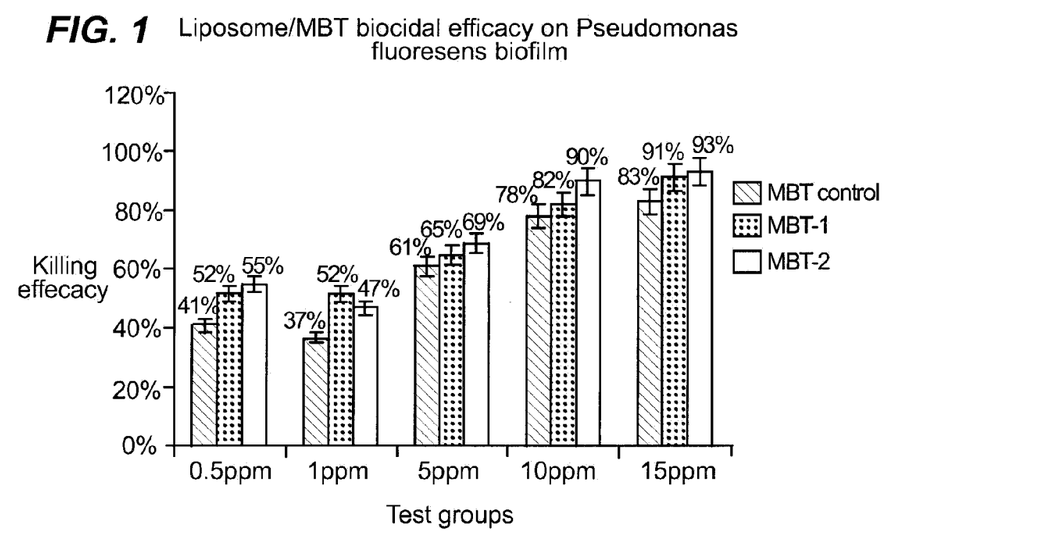
FIG. 1 shows the results in graph form of the efficacy of liposome/ethylene bis thiocyanate (MBT) at various concentrations.
Figure 2:
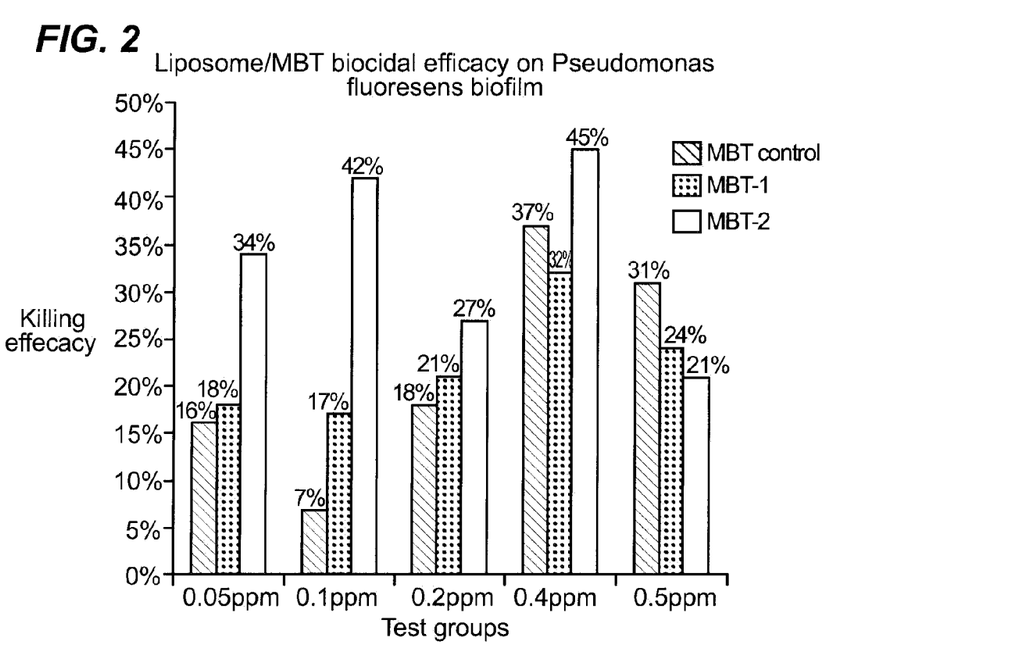
FIG. 2 shows the results in graph form of the efficacy of liposome/methylene bis thiocyanate (MBT) at various concentrations.
Figure 3:
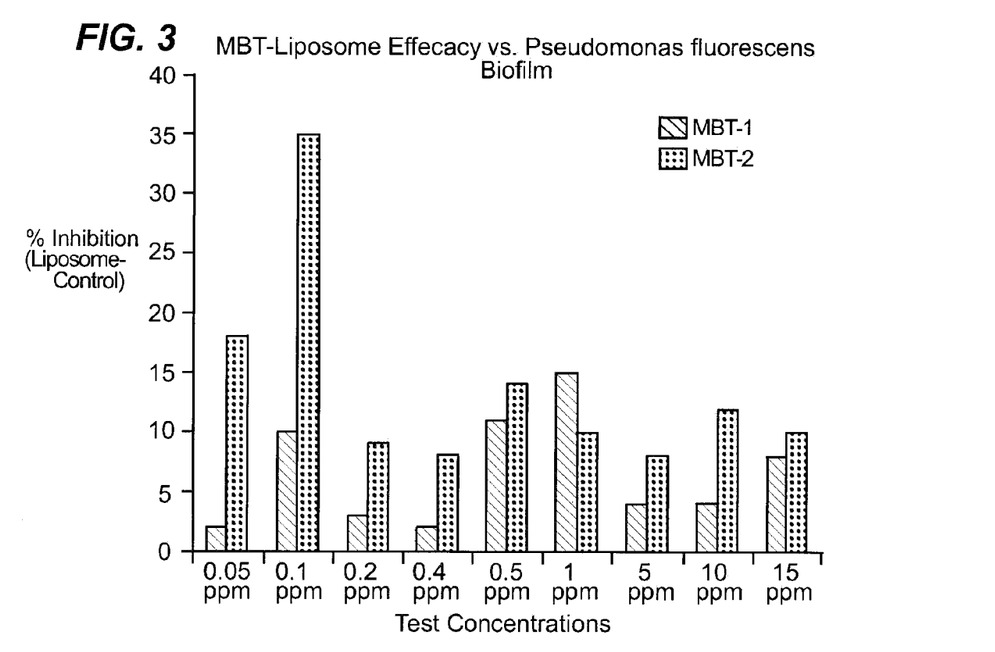
FIG. 3 shows the results in graph form of the efficacy of liposome/MBT at varying concentrations.

The results are shown in the FIGS. 1, 2, and 3. The non-liposomal MBT is listed as the MBT Control. It is clear from the figures that both liposomal-MBT formulations had better biofilm killing/removal efficiency than the MBT control in the majority of the liposome concentrations that were tested, the exception being with the highest MBT concentration tested. At the high concentration of MBT (0.5 ppm), the use of a liposome as a carrier for the biocide becomes unnecessary. The liposome carrier is highly effective at delivering biocide to the biofilm at low MBT concentrations, thus providing better biofilm control at much reduced MBT concentrations (reduced toxicity and cost performance).

Figure 4:
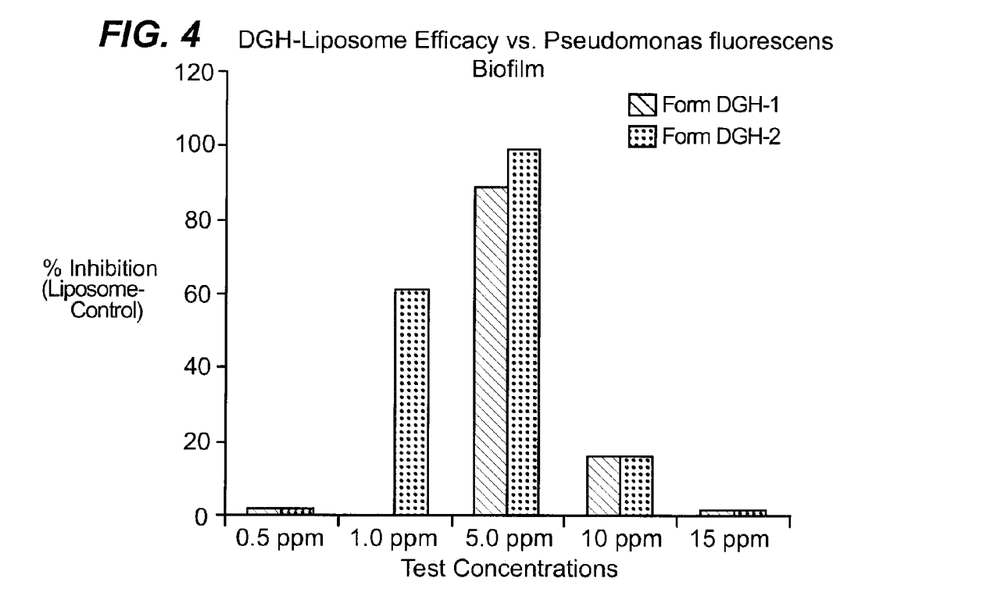
FIG. 4 shows the results in graph form of the efficacy of two decylguanidine hydrochloride (DGH)/liposome formulations at varying concentrations.

Two dodecylguanidine hydrochloride (DGH) liposome formulations were also created and designated FORM DGH-1 and FORM DGH-2. These liposome formulations were also evaluated against *Pseudomonas fluorescens* biofilms and compared in efficacy to a non-liposome DGH at the same concentration. These results are shown in FIG. 4. Both of these liposome-DGH formulations showed greater efficacy than the control DGH against the *Pseudomonas* biofilm, particularly in the 0.0 to 10 ppm concentration range.

In one exemplary embodiment, fouling of the aqueous system is controlled such as by killing, reducing, removing, or inhibiting the growth of, or inactivating the biofilm. In one embodiment, the vesicle, such as a liposome vesicle, contains a biofilm control agent that, when released from the vesicle upon incorporation of the vesicle into the biofilm matrix, reacts with the encased or entrapped microorganism to kill, reduce, remove, or inhibit the growth of or inactivate the microorganism. The polysaccharide/protein matrix of the biofilm thereby decomposes to result in reduced fouling of the aqueous system.

In one embodiment, the biofilm control agent reacts with the encased microorganisms to kill or substantially remove them. In another embodiment, the biofilm control agent reacts with the encased microorganisms to interfere with their life or reproductive cycles to arrest or inhibit the growth of the microorganisms.

In one aspect of the invention, the biofilm control agent that is contained within the liposome vesicle may comprise a biocide or non-biocidal agent for controlling the biofilm. In one embodiment of the invention, the biofilm control agent is encapsulated in a micro-capsule, nano-capsule, or other vesicle, and then the vesicle containing the biofilm control agent is added to the requisite aqueous system to control fouling by killing, reducing, removing, inhibiting the growth of, or inactivating the microorganisms encased in the biofilm. As the vesicle decomposes, such as by digestion, the biofilm control agent, comprising a biocide or non-biocidal agent, is released to act on the microorganisms encased or entrapped by the biofilm matrix.

The micro-capsule or nano-capsule is a microscopic vesicle or type of structure that encloses a biocide or non-biocidal agent and is adapted for delivering the biocide or non-biocidal agent to the biofilm in an aqueous system. In one embodiment, the micro-capsule or nano-capsule contains the biocide or non-biocidal agent within its core. The micro-capsule or nano-capsule may be produced by any known process and has a similar composition of a microbial membrane and size of a microbial cell and is produced such that it has an exterior composition adapted for decomposition when in contact with the biofilm matrix. In one embodiment, the micro-capsule or nano-capsule may be prepared from material, such as lecithin, gums, gels, biodegradable or non-biodegradable polymers, such as polylactic acid or polystyrene, organic polymers, combinations of lecithin and organically functionalized lecithin where the functionalization can either be polymer chains, peptides, proteins, lipids, cholesterols or bio receptors. The material may also be multi-block polymers containing hydrophobic and hydrophilic blocks, self-assembled Donor:Acceptor moieties and micelles, inorganic spheres, rods, cages or particles.

The micro-capsules or nano-capsules are produced and applied in any size suitable for decomposition or programmed disintegration thereof. In one embodiment, the micro-capsule or nano-capsule may be from about 0.01 micron to about 100 microns. In another embodiment, the micro-capsule or nano-capsule has a size of from about 0.01 micron to about 50 microns. In another embodiment, the micro-capsule or nano-capsule has a size of from about 0.01 micron to about 20 microns. In another embodiment, the micro-capsule or nano-capsule has a size of from about 0.05 micron to about 15 microns. In another embodiment, the micro-capsule or nano-capsule has a size of from about 0.1 micron to about 10 microns. In another embodiment, the micro-capsule or nano-capsule has a size of from about 0.25 micron to about 2 microns. The size of the micro-capsules or nano-capsules is measured directly by microscopic techniques.

Micro-capsules or nano-capsules can be manufactured by any known process, including, but not limited to, controlled evaporation, extrusion, such as pressure extrusion of an aqueous biocide or non-biocidal agent through a porous membrane into the micro-capsule or nano-capsule body, injection, sonication, microfluid processors and rotor-stator mixers. In one embodiment, the material for the micro-capsule or nano-capsule is added to an aqueous solution containing a biocide or non-biocidal agent and forms a vesicle containing the biocide or non-biocidal agent. Exemplary processes for preparing liposome vesicles are disclosed in U.S. Pat. Nos. 5,807,572 and 7,491,409, both hereby incorporated by reference herein.

In one embodiment, the micro-capsule or nano-capsule forms a bilayer or multilayer vesicle. For example, the biocide or non-biocidal agent may be encapsulated within other materials by known encapsulation processes, so as to have one or more protective outer layers that define the micro-capsule or nano-capsule lifetime, delivery characteristics, and use environment. In one embodiment, the biocide or non-biocidal agent is within the aqueous core of the micro-capsule or nano-capsule. In another embodiment, the biocide or non-biocidal agent may be injected into the micro-capsule or nano-capsule and carried in one of the layers of the micro-capsule or nano-capsule.

The biocide may be any type of biocide that is suitable for killing or destroying the microorganisms that are in contact with the biofilm. In one embodiment, the biocide may be a non-oxidizing, oxidizing or molluscicide antimicrobial compound, or combinations thereof. In another embodiment, the biocide includes, but is not limited to, guanidine or biguanidine salts, quaternary ammonium salts, phosphonium salts, 2-bromo-2-nitropropane-1,3-diol, 5-chloro-2-methyl-4-isothiazolin-3-one/2-methyl-4-isothiazolin-3-one, n-alkyl-dimethylbenzylammonium chloride, 2,2,dibromo-3-nitrilo-propionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium salt, 4,5,-dichloro-1,2,-dithiol-3-one, sodium dimethyldithiocarbamate, disodium ethylenebisdithiocarbamate, Bis(trichloromethyl) sulfone, 3,5-dimethyl-tetrahydro-2H-1,3,5,-thiadiazine-2-thione, 1,2,-benzisothiazolin-3-one, decylthioethylamine hydrochloride, copper sulfate, silver nitrate, colloidal silver, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, dibromo, dicyano butane and combinations thereof.

In one embodiment, the biocide may be guanidine or biguanidine salts, quaternary ammonium salts and phosphonium salts. Examples of guanidine or biguanidine salts are of the general formulas:

wherein R, $R^1$, $R^2$ are independently H, $C_1$-$C_{20}$ substituted or non-substituted alkyl (linear or branched) or aryl, X is an organic or inorganic acid, n is 0-20 and z is 1-12.

Examples of the general formula of acceptable phosphonium salts comprises $(R_1)_3P^+R_2.X^-$ wherein $R_1$ is an alkyl group of from 1 to 8 carbon atoms, $R_2$ is an n-alkyl group giving 8 to 20 carbon atoms, and X is an anion consisting of a halide, sulfate, nitrate, nitrite, and combinations thereof.

An alternative formula provides that $R_1$ is an alkyl group having from 1-8 carbons, $R_2$ is an n-alkyl group having 6-20 carbon groups, and $X^-$ is an anion such as halides, sulfates, nitrates, nitrites and mixtures thereof. Preferably, $X^-$ is chloride, bromide, iodide, $SO_4^-$, and $NO_3^-$, $NO_2$ or mixtures thereof.

Another embodiment provides R1 and R2 are hydroxyalkyl groups having from 1-4 carbons and $X^-$ is an anion such as halides, sulfates, nitrates, nitrites and mixtures thereof. Preferably, $X^-$ is chloride, bromide, iodide, $SO_4^=$, and $NO3^-$, $NO2^-$ or mixtures thereof.

Quaternary ammonium salts are another example of a biocide or agent that may be encapsulated or manufactured into a liposome core, and are of the general formula wherein $R_1$ is an n-alkyl group of chain length $C_8$-$C_{18}$; $R_2$ and $R_3$ are $CH_3$ or n-alkyl group of chain length $C_2$-$C_8$ and $X^-$ is an anion such as halides, sulfates, nitrates, nitrites and mixtures thereof.

The non-biocidal agents may be any type of environmentally friendly compound or composition that removes or inactivates the microorganisms encased or entrained in the biofilm to keep them from spreading, such as by interfering with their life or reproductive cycles. In one embodiment, the non-biocidal agent may be used as an adjuvant with a biocide. For example, non-biocidal agents include, but are not limited to, biodispersants, ethylene oxide/propylene oxide copolymers, trichlorohexanoic acid, polysiloxanes, carbosilanes, polyethyleneimine, bacteria, microorganisms, plasmids, phagocytes, macrophages, toxin-producing microorganisms, viruses, amino acids, proteins, peptides, DNA, RNA, base pairs, antisense RNA, pharmaceuticals, antibiotics, chelators, natural extracts, organic/inorganic redox agents, organic and inorganic dye sensitizers, apoptosis signaling reagent, microorganism- and plant-derived extracts and by-products, metabolic components, preservatives, toxic phytochemicals, microbial toxins, catalysts that generate free radicals or active oxygen species, L-cystin and enzymes or combinations thereof.

In addition to the incorporation of the biofilm control agent in the vesicle, stabilizing agents may also be included to increase product shelf life. The stabilizing agents render the vesicle/biofilm control agent combination less prone to chemical decomposition and inhibit physical phase separation of the components. In one exemplary embodiment, the stabilizing agent is a buffer consisting of a citrate salt, a chlorate salt buffer, and an acetate salt. The stabilizer compound buffer may be comprised of a mixture of two or more compounds selected from the group consisting of the metal salt of a citrate/chlorate buffer, a metal salt of an acetate/chlorate buffer, and a citrate/acetate buffer. The buffer stabilizer may be selected from the group consisting of a sodium citrate buffer, a sodium acetate buffer, a sodium citrate/sodium chlorate buffer mixture, and a sodium acetate/sodium chlorate buffer mixture. The buffer stabilizer may be incorporated with the biofilm control agent in an amount from about 0.2% to about 10% of the total biofilm control agent/liposome vesicle composition, and more preferably, the control agent may be incorporated in an amount of about 1.0 wt % to about 12.0 wt % of the total biofilm control agent/liposome vesicle composition. Even more specifically, the control agent may be incorporated in an amount of about 10.0 wt % to about 12.0 wt % of the total biofilm control agent/liposome vesicle composition. The liposome vesicle structure may be up to about 200 microns in diameter and preferably, is between about 100 nanometers to about 10 microns in diameter.

The industrial system may be an aqueous system. The industrial system can be chosen from the group consisting of water distribution systems, cooling towers, boiler systems, showers, aquaria, sprinklers, spas, cleaning bath systems, air washers, pasteurizers, air conditioners, fluid transporting pipelines, storage tanks, ion exchange resins, food and beverage processing lines, paint spray booths, metalworking fluid baths, coal and mineral slurries, metal leaching fluids, wastewater treatment facilities, pulping and papermaking suspensions, mollusk control, acid mine drainage, oil drilling pipes, oil pipelines, oil storage tanks, gas drilling pipes, gas pipelines, or any industrial application prone to microbial induced bio-film formation or microbial induced corrosion.

In addition to the exemplary stabilizing agents noted above, additional stabilizing agents that may be mentioned include:

a) $KIO_3$, $HIO_3$, periodic, periodate salts
b) metal nitrates—Na, K, Ca, Mg
c) orthoesters—trimethyl orthoformate, triethyl orthoformate, triethyl orthoacetate, trimethyl orthovalerate, trimethyl orthobenzoate
d) formaldehyde releases
e) phenoxyalkanols—phenoxyethanol, phenoxy isopropanol
f) nitrogen based heterocyclic thiols—2 mercapto pyridine, MTZ, 2-thiohydantoin, L-cystin
g) EDTA or other chelators
h) rheological modification agents such as thickeners
i) stearic hindrance agents (long chain repulsive)
j) yield value modification polymer as (suspending agent)
k) Tween, Triton, alcohol ethoxylates or other dispersants and surface acting agents The biofilm control agent and stabilizer may, in one aspect of the invention, be incorporated into the vesicle in any amount sufficient for controlling the microorganism encased in the biofilm matrix and will depend on the specific biofilm control agent and stabilizer chosen.

In one embodiment, the biofilm control agent is incorporated into a liposome vesicle in an amount of about 1.0 wt %-12 wt %, and the stabilizer is added to the vesicle in an amount of 0.02 wt %-10.0 wt %.

While the present invention has been described with references to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but also all that fall within the scope of the appended claims.

The invention claimed is:

1. A process for controlling fouling of an aqueous system including a biofilm matrix and microorganisms in contact with said matrix, said process comprising:
providing a biofilm control agent in a vesicle, wherein said vesicle is prepared from lecithin and/or multiblock polymers and wherein said vesicle contains a stabilizing agent wherein said stabilizing agent is a buffer comprising a mixture of two or more compounds selected from the group consisting of a citrate salt, a chlorate salt and an acetate salt; and
adding said vesicle to said aqueous system whereby said vesicle is incorporated into said biofilm and releases said biofilm control agent to contact said microorganisms.

2. Process as recited in claim 1 wherein said stabilizing agent is a buffer comprising a mixture of two or more compounds selected from the group consisting of the metal salt of a citrate/chlorate buffer, a metal salt of an acetate/chlorate buffer, and a citrate/acetate buffer.

3. Process as recited in claim 1 wherein said buffer is selected from the group consisting of a sodium citrate buffer, a sodium acetate buffer, a sodium citrate/sodium chlorate buffer mixture, and a sodium acetate/sodium chlorate buffer mixture.

4. The process of claim 1, wherein said multiblock polymers contain hydrophobic and hydrophilic blocks.

5. A process for controlling fouling of an aqueous system including a biofilm matrix and microorganisms in contact with said matrix, said process comprising:
providing a biofilm control agent in a vesicle, said vesicle containing a stabilizing agent wherein said stabilizing agent is a buffer comprising a mixture of two or more compounds selected from the group consisting of a citrate salt, a chlorate salt and an acetate salt; and
adding said vesicle to said aqueous system whereby said vesicle is incorporated into said biofilm and releases said biofilm control agent to contact said microorganisms.

6. Process as recited in claim 5 wherein said stabilizing agent is a buffer comprising a mixture of two or more compounds selected from the group consisting of the metal salt of a citrate/chlorate buffer, a metal salt of an acetate/chlorate buffer, and a citrate/acetate buffer.

7. Process as recited in claim 5 wherein said buffer is selected from the group consisting of a sodium citrate buffer, a sodium acetate buffer, a sodium citrate/sodium chlorate buffer mixture, and a sodium acetate/sodium chlorate buffer mixture.

8. Process as recited in claim 5 wherein said biofilm control agent comprises a biocide or non-biocidal agent.

9. Process as recited in claim 8 wherein said biofilm control agent is a biocide and said biocide is a non-oxidizing, oxidizing, or molluscicide antimicrobial compound.

10. Process as recited in claim 8 wherein said biofilm control agent is a biocide and said biocide is chosen from the group consisting of 2-bromo-2-nitropropane-1,3-diol, 5-chloro-2-methyl-4-isothiazolin-3-one/2-methyl-4-isothiazolin-3-one, n-alkyl-dimethylbenzylammonium chloride, 2,2-dibromo-3-nitrilopropionamidemethylene-bis(thiocyanate), dodecylguanidine hydrochloride, glutaraldehyde, 2-(tert-butylamino)-4-chloro-6-(ethylamino)-s-triazine, beta-bromonitrostyrene, tributyltinoxide, n-tributyltetradecyl phosphonium chloride, tetrahydroxymethyl phosphonium salt, 4,5-dichloro-1,2-dithio-3-one, sodium dimethyldithiocarbamate, disodium ethylenebisdithiocarbamate, Bis(trichloromethyl) sulfone, 3,5-dimethyl-tetrahydro-2H-1,3,5-thiadiazine-2-thione, 1,2-benzisothiazolin-3-one, decylthioethylamine hydrochloride, copper sulfate, silver nitrate, colloidal silver, bromochlorodimethylhydantoin, sodium bromide, dichlorodimethylhydantoin, sodium hypochlorite, hydrogen peroxide, chlorine dioxide, sodium chlorite, bromine chloride, peracetic acid and precursors, sodium trichloroisocyanurate, sodium trichloroisocyanurate, dibromo, dicyano butane and combinations thereof.

11. Process as recited in claim 8 wherein said biofilm control agent is a non-biocidal agent, said non-biocidal agent being chosen from the group consisting of biodispersants, ethylene oxide / propylene oxide copolymers, trichlorohexanoic acid, polysiloxanes, carbosilanes, polyethyleneimine, bacteria, microorganisms, plasmids, phagocytes, macrophages, toxin-producing microorganisms, amino acids, proteins, peptides, DNA, RNA, base pairs, antisense RNA, pharmaceuticals, antibiotics, chelators, natural extracts, organic/inorganic redox agents, organic and inorganic dye sensitizers, apoptosis signaling reagent, microorganism- and plant-derived extracts and by-products, metabolic components, preservatives, toxic phytochemicals, microbial toxins, catalysts that generate free radicals or active oxygen species, L-cystin and enzymes or combinations thereof.

12. Process as recited in claim 5 wherein said vesicle is composed of a liposome.

13. The process of claim 5 wherein said vesicle is produced in sizes from about 0.05 to about 15μ.

14. The process of claim 13 wherein said vesicle is produced in sizes from about 0.1 to about 10μ.

15. The process of claim 5 wherein said vesicle is a liposome vesicle and said biofilm control agent is incorporated into said liposome vesicle in an amount of about 0.05 to about 5.0 grams control agent active per gram lipid.

16. The process of claim 15 wherein said biofilm control agent is incorporated into said liposome in an amount of from 0.1 to about 2.0 grams biofilm control agent active per gram lipid.

17. The process of claim 5 wherein said vesicle is a liposome vesicle and wherein said biofilm control agent is added to said aqueous system in an amount of from about 0.01 ppm to about 100 ppm.

18. The process of claim 5 wherein said aqueous system is chosen from the group consisting of water distribution systems, cooling towers, boiler systems, showers, aquaria, sprinklers, spas, cleaning baths systems, air washers, pasteurizers, air conditioners, fluid transporting pipelines, storage tanks, ion exchange resins, food and beverage processing lines, metalworking fluid baths, coal and mineral slurries, metal leaching fluids, wastewater treatment facilities, mollusk control, acid mine drainage, or any application prone to biofouling by microbial species.

19. The process of claim 5 wherein said aqueous system is chosen from the group consisting of anti-corrosion treatments, hormone, vitamin or anti-oxidant treatments, antibiotic and gene therapies, pesticides for agriculture and commercial home uses, food additives and preservatives, chemical and biological detection, color and flavor enhancement, odor control and aquatic pest management.

\* \* \* \* \*